(12) United States Patent
Contrada et al.

(10) Patent No.: US 7,098,660 B2
(45) Date of Patent: Aug. 29, 2006

(54) DIAGNOSTIC IMAGING APPARATUS AND METHOD FOR LIMBS, PARTICULARLY THE HAND BY MEANS OF NUCLEAR MAGNETIC RESONANCE

(75) Inventors: Orfeo Contrada, Genoa (IT); Luigi Satragno, Genoa (IT)

(73) Assignee: Esaote S.p.A., Casale Monferrato (IT)

( * ) Notice: Subject to any disclaimer, the term of this patent is extended or adjusted under 35 U.S.C. 154(b) by 91 days.

(21) Appl. No.: 10/928,151

(22) Filed: Aug. 30, 2004

(65) Prior Publication Data
US 2005/0090734 A1   Apr. 28, 2005

(30) Foreign Application Priority Data
Sep. 9, 2003  (IT) .......................... SV2003A0033

(51) Int. Cl.
*G01V 3/00* (2006.01)
(52) U.S. Cl. ...................... 324/318; 324/309
(58) Field of Classification Search ................ 324/318, 324/319, 320, 309, 322, 307, 300; 600/410; 335/301
See application file for complete search history.

(56) References Cited

U.S. PATENT DOCUMENTS

| | | | | |
|---|---|---|---|---|
| 598,631 A | * | 2/1898 | Carozzi ...................... | 52/592.1 |
| 4,674,110 A | | 6/1987 | Eaton et al. | |
| 5,657,369 A | | 8/1997 | Stein et al. | |
| 5,986,531 A | * | 11/1999 | Carrozzi ...................... | 335/301 |
| 6,459,927 B1 | | 10/2002 | Franklin et al. | |
| 6,490,473 B1 | * | 12/2002 | Katznelson et al. ......... | 600/410 |
| 6,586,934 B1 | * | 7/2003 | Biglieri et al. ............... | 324/309 |
| 6,684,096 B1 | * | 1/2004 | Schmit et al. ............... | 600/415 |
| 6,822,447 B1 | * | 11/2004 | Yamagata .................... | 324/318 |
| 6,882,878 B1 | * | 4/2005 | Schmit et al. ............... | 600/415 |
| 2002/0077539 A1 | | 6/2002 | Schmit et al. | |
| 2002/0103428 A1 | | 8/2002 | deCharms | |

FOREIGN PATENT DOCUMENTS

| | | |
|---|---|---|
| EP | 0 930 510 A2 | 7/1999 |
| WO | 79/00779 A1 | 10/1979 |
| WO | 02/22013 A1 | 3/2002 |

\* cited by examiner

*Primary Examiner*—Brij B. Shrivastav
(74) *Attorney, Agent, or Firm*—Buchanan Ingersoll & Rooney PC

(57) ABSTRACT

A method and apparatus for diagnostic imaging of a body part, by nuclear magnetic resonance, which method includes the steps of positioning the body part in a detection volume of a nuclear magnetic resonance imaging apparatus, inside a dedicated receiving coil; selecting the section or sections of said body part that has to be imaged and carrying out image detection by nuclear magnetic resonance; identifying and storing the detected images; and carrying out at intervals one or more subsequent image detections with nuclear magnetic resonance of the same body part and of the same section thereof as in the preceding image detections with nuclear magnetic resonance, positioning each time the body part in the same relative position with respect to the imaging volume of the nuclear magnetic resonance imaging apparatus.

26 Claims, 5 Drawing Sheets

DIAGNOSTIC IMAGING APPARATUS AND METHOD FOR LIMBS, PARTICULARLY THE HAND BY MEANS OF NUCLEAR MAGNETIC RESONANCE

CROSS-REFERENCE TO RELATED APPLICATIONS

The present application claims the priority of Italian Patent Application No. SV2003A000033, filed in Italy on Sep. 9, 2003, the entire content of which is incorporated herein by reference.

BACKGROUND OF THE APPLICATION

1. Field of the Invention

The present invention relates to a diagnostic imaging apparatus and method for limbs, particularly the hand, by means of nuclear magnetic resonance, which method comprises the steps of positioning the hand in a detection volume of a nuclear magnetic resonance imaging apparatus, inside a dedicated coil, of selecting the section or sections of the hand or wrist of which the image has to be detected and of carrying out the image detection by means of nuclear magnetic resonance.

2. Discussion of Related Art

At present it has been found that in the evaluation of rheumatoid arthritis the images detected by nuclear magnetic resonance allow one to visualize pathological damages caused by rheumatoid arthritis in a better way than radiograph images, particularly the so called erosion. However these damages are at an advanced phase of the pathology. Recent analysis have shown that due to the image detection with nuclear magnetic resonance it is possible to find damages caused by rheumatoid arthritis in the initial phases of the pathology, such as the damage of soft tissues for example synovium, tendons and meniscus.

The synovial membrane is the main inflammation site in the precocious phases of rheumatoid arthritis. During these phases the inflammatory action involves an increase of the vascularization that can be highlighted in the nuclear magnetic resonance images by means of proper contrast agents, such as Gadolinium-di ethylentriamine of pentacetic acid (Gd-DTPA). Recording time sequences of nuclear magnetic resonance images of the synovial membrane with the above contrast agents shows changes of the signal intensity as a function of time that can be considered as indicators of the synovial inflammation and of the pathological activity. This has been shown by analysis regarding the intensity changes of MRI signal in the synovial membrane of the wrist.

OBJECTS AND SUMMARY

On the basis of the analysis carried out on different patient groups having different pathology activities and patient groups in the recovery phase, at least one embodiment of the present invention provides a method for the progressive evaluation of the pathology course. The method comprises the imaging steps disclosed hereinbefore and one or more subsequent nuclear magnetic resonance image detections of the same part and of the same section thereof as in a preceding nuclear magnetic resonance image detection, each time repositioning the anatomic part, particularly the limbs and especially of the hand in the same relative position with respect to the imaging volume of the nuclear magnetic resonance imaging apparatus.

The method provides also a storage of nuclear magnetic resonance image detection sequences used in the preceding detecting sessions, of doses and administration modes of the contrast agents and particularly the definition of the section plane or planes along which the nuclear magnetic resonance images are detected.

The method provides that the repositioning is carried out by using means that assure a millimetric and even sub-millimetric positioning repeatability.

The invention relates also to an apparatus that allows said repeated positioning.

Repositioning means may be an electronic type, i.e., it can use the capability of the nuclear magnetic resonance apparatus or it can be different electronic means such as telecamera or space sensor of markers applied on the limb in positions anatomically sure.

According to a preferred example that is very economical, user-friendly and of sure length and efficacy and that allows an extremely precise positioning, said means are composed of a receiving coil to which a cast of the patient limb, particularly the hand, is coupled.

The cast is advantageously of the cylindrical type and encloses the hand and the wrist and at least part of the forearm on all sides and is of the type that can be opened.

As regards the register repositioning of at least two cast portions, it is possible to use the repositioning means typical of casts and well known.

The cast has precise positioning and centering means at least with respect to a supporting bracket having precise positioning means in the apparatus for nuclear resonance magnetic imaging apparatus.

According to an advantageous feature, the bracket is composed of the bracket of the receiving coil and the receiving coil itself.

Particularly, the cast can be made in a die having a shape exactly identical to the shape of the bracket and the receiving coil outside the nuclear magnetic resonance apparatus.

Otherwise, the bracket itself and the receiving coil can form the die making the cast that can be directly made with the coil positioned inside the nuclear magnetic resonance imaging apparatus and preferably after having properly positioned the hand with respect to the image detection volume of the apparatus itself.

For the above aims it is advantageous to use a receiving coil of cylindrical annular or elliptical type associated to a coaxial or concentric bracket that together with the annular coil forms a box or case that can be opened and tight closed functioning as a die.

The cast portions may be made detachable to the bracket and the receiving coil, reciprocal centering means being provided of movable type and that are generated and incorporated inside the cast walls when it is moulded.

In an alternative example, the coil and the bracket are made by at least two portions hinged one with respect to the other along the same axis, said two portions being associable each to one of two cast portions and said cast portions being attached in place by means of movable fastening means, while due to the hinging means of said two bracket and receiving coil portions it is possible to bring said two bracket and coil portions and the associated cast portions from an opened position of the cast and an introduction position of the limb to a closed position of said two portions and to a clamping position without substantial compressive force but with a sure clamping in place of the limb simultaneously inside the cast and inside the receiving coil and/or also inside the bracket.

As regards the material that is used to form the cast, it can be any suitable material having the required features of permeability to the excitation and receiving RF signal without generating substantial changes on the same and/or without generating noises to the nuclear resonance magnetic imaging apparatus.

Systematic and constant noises or aberrations may be tolerated if they do not involve decadences of the image quality due to systematic adjustments implementable in the nuclear magnetic resonance imaging apparatus.

On the basis of what is set out above it is possible to follow analytically and with objective quantitative and precise means the course of the rheumatoid arthritis in end limbs or in extremities and particularly in the hand or in the wrist. That can occur starting from young phases of the pathology before the damages caused by it can be of considerable level.

Therefore the methods according to the present invention allows one to evaluate objectively and in a sure scientific way the course itself allowing to intervene in a proper manner to correct the course itself that due to the repositioning of the limb at time intervals in the same image detection position with respect to the preceding detection positions.

The precise positioning means can be of any type. The preferred embodiments shown herein are characterized by a simple construction but really efficient in guaranteeing the precise repositioning position. Possible not traumatic changes in time of the hand anatomy have been analyzed and unexpectedly it has been found that their effect is almost of no value on the proper positioning and that therefore such effects are not important.

One embodiment according to the present invention combines the receiving coil with its supporting bracket with the repositioning means composed of a cast. The cast is obtained by means of simple casting manufacture in a die that has contact surfaces with the cast having the same shape and size as the ones provided on the receiving coil and on the relative supporting bracket.

Advantageously the construction of the coil and of the supporting bracket can be such to form themselves the casting die for making the cast, improving the positioning accuracy and above all knocking down prices and making the operations even simpler and faster.

BRIEF DESCRIPTION OF THE DRAWINGS

The characteristics of the invention and the advantages derived therefrom will appear more clearly from the following description of a few nonlimiting embodiments illustrated in the annexed drawings. In which.

DETAILED DESCRIPTION OF THE PREFERRED EMBODIMENTS

Figure 1:
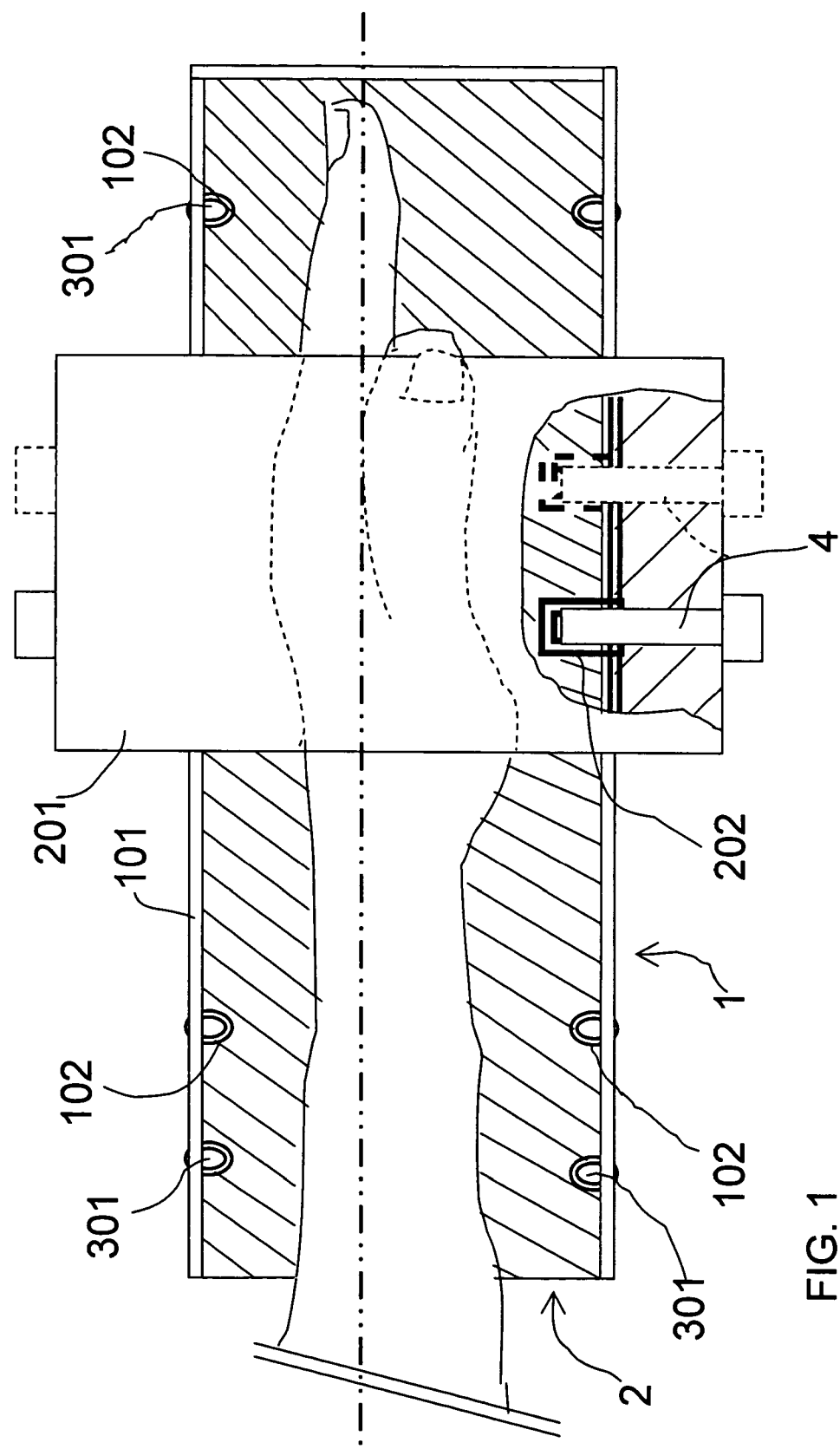
FIG. 1 is a part section top plan view of an apparatus for repositioning the hand and the wrist according to an embodiment of the present invention.

Referring to the figures, a device for properly positioning the hand according to a preferred embodiment of the present invention includes the combination of a hand supporting bracket and a receiving coil assembly generally indicated by 1 and the cast of the hand itself indicated by 2 and shown in axial section. A bracket 101 is composed of a lower part 101' bearing the hand that can extend in the direction of the forearm to such extent up to the wrist and beyond it in the direction of the elbow. Said lower part 101' is made with a concave surface with an arched section, particularly a circular one and extending for such angular width substantially of 180° C.

The bracket 101 extends inside an annular receiving coil 201 closed on itself and extending only for a partial axial length of the total length of the bracket 101.

The hand cast 2 is in the interior for the total length of the bearing lower part 101' or for only a part thereof, preferably for the part substantially coincident with the receiving coil 201. The hand cast 2 is preferably divided into two halves along an axial plane that is coincident or parallel to a central axial section plane and which plane is parallely oriented to the plane defined by the extension of the hand. The cast 2 can have predetermined centering means with the bearing lower part 101' of the bracket 101 of the limb and of the receiving coil 201 and with the annular receiving coil itself.

In this case, in the supporting lower part 101' along the internal contact side with the cast, one or more coaxial ribs 301 are provided engaging with corresponding grooves 102 of the cast. Alternatively, the opposite arrangement may be provided.

A coupling and centering means of the cast with the receiving coil can be composed of radial holes in said annular coil that are coincident with radial dead holes 202 provided in coincident and predetermined positions in the cast portions and of fastening and centering pins, screws or bolts 4 engaging the holes of the cast through the annular wall of the receiving coil. It is possible to provide several such pins and holes distributed along the coil circumference as highlighted with discontinuous lines.

In this embodiment, the cast may be made outside the receiving coil, i.e., of the supporting means and receiving coil assembly, in a device that is shaped in an identical way to the structure of the coil and supporting bracket.

In this case, movable walls are provided completing the lower part with a top part and therefore enclosing on all sides a chamber necessary for containing the plaster, resin or other casting material. At least one of the two head sides obviously can not be closed with a wall because the forearm comes out therefrom. In this case it can be assumed a closing by means of a resilient relatively soft seal or by means of an annular seal that can be swollen fitting the annular gap that is free between the forearm and the delimitating wall of the chamber for the casting. The opposite head side can be closed in a similar manner if the hand projects beyond the bracket or it can be simply closed by a head wall when the hand ends before the corresponding head edge of the bracket 101.

Figure 2:
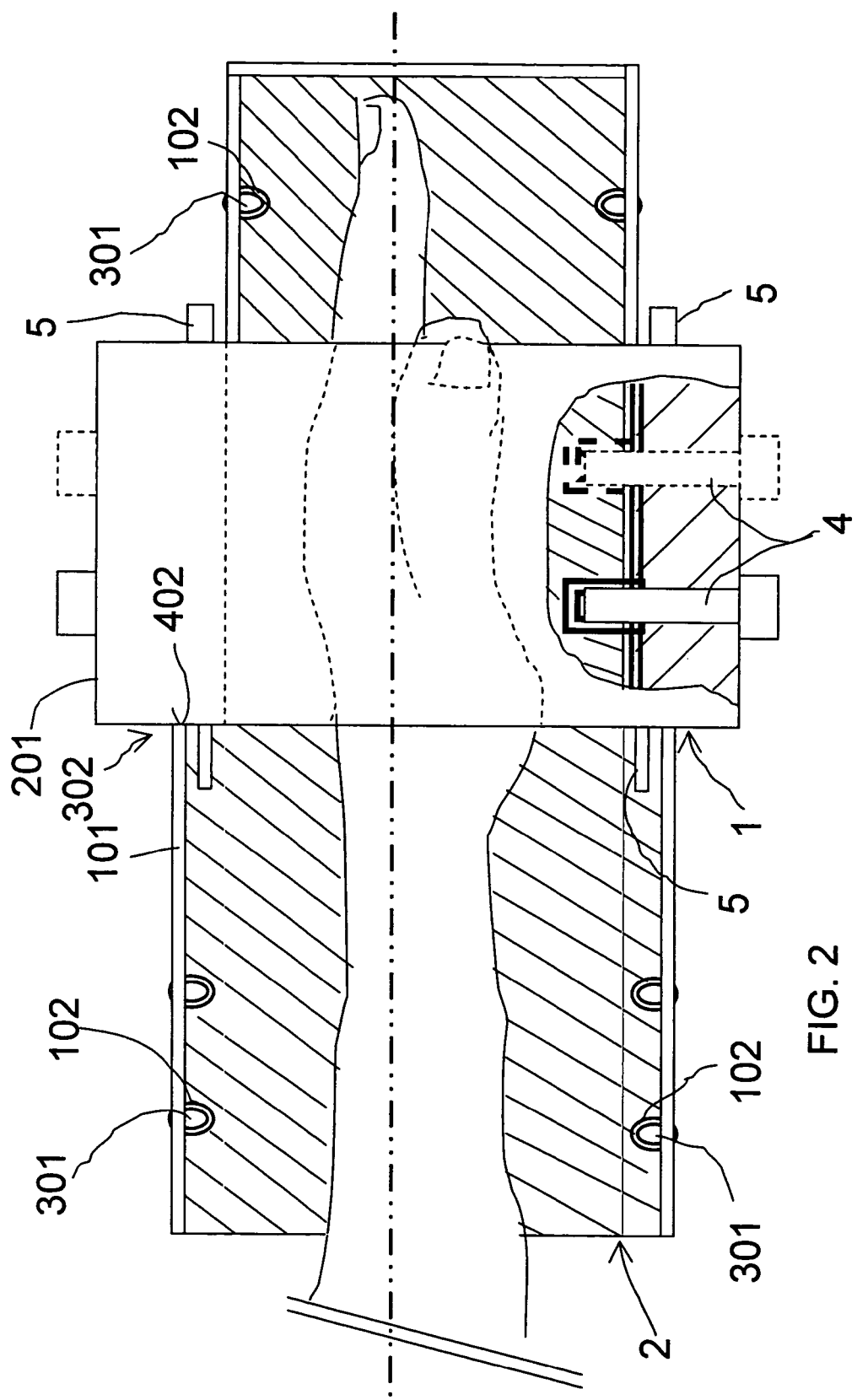
FIG. 2 is a variant of the apparatus of FIG. 1.

FIG. 2 shows another embodiment wherein further abutment surfaces are provided for the proper reciprocal positioning between the cast 2 and the assembly 1 composed of the bracket and the receiving coil. In this case the cast portion projecting on the introduction side of the forearm is realized with a larger diameter with respect to the inner diameter of the annular receiving coil 201 and it forms a step 302 with an axial annular abutment surface 402 against the faced annular head side of the receiving coil 201 itself.

Figure 3:
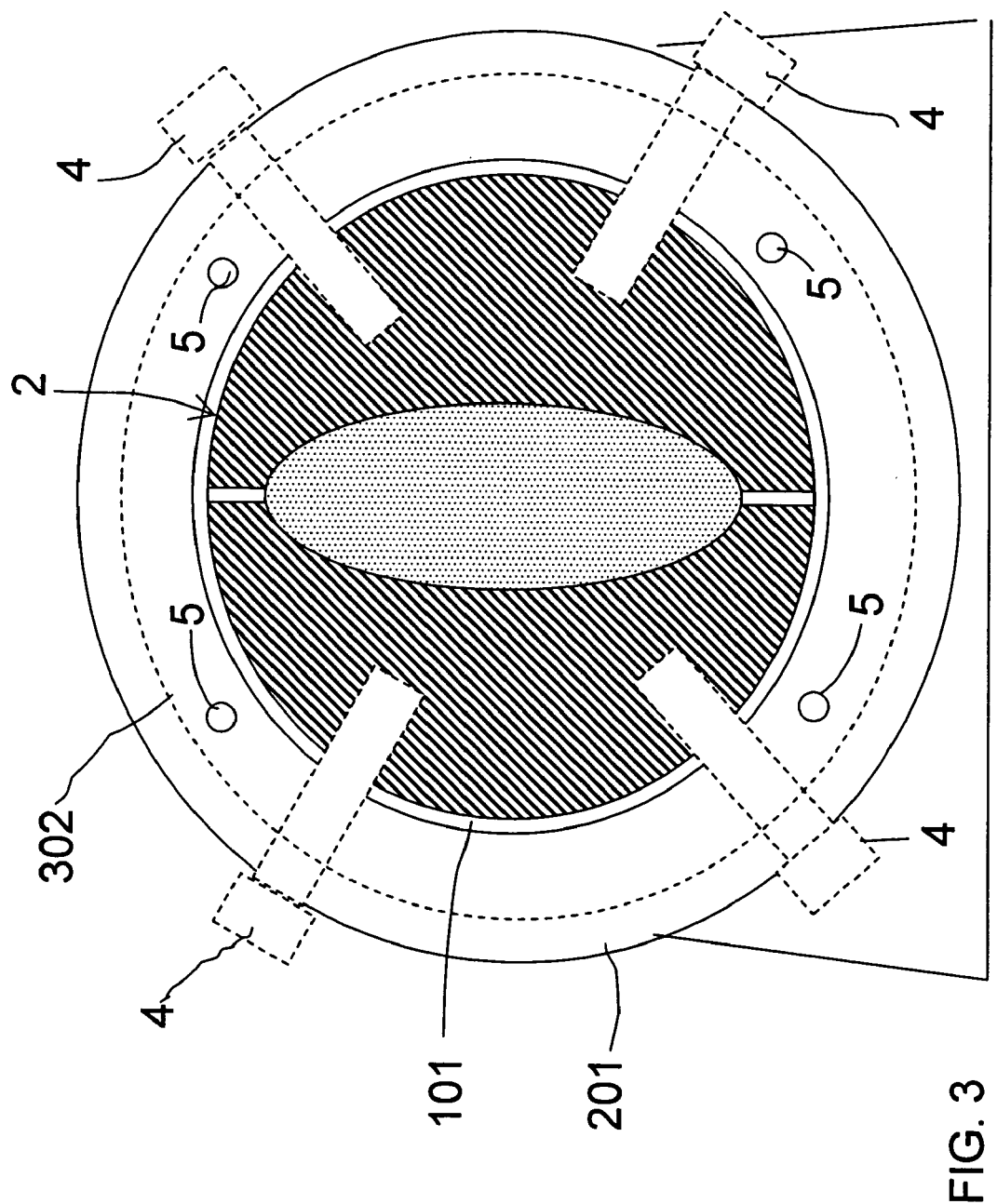
FIG. 3 is a front view with the cast in transverse section of the apparatus according to the preceding figures.

Such surface is highlighted also in FIG. 3, the same being indicated with a circular discontinuous line. Within the radial width of the axial abutment surface 402 axial centering means 5 may be provided which can be composed of one or more axial pins 5 arranged along the circumference. In the illustrated example, the axial pins 5 pass through the axial thickness of the coil 201, but this is only one of the many construction arrangements that a person skilled in the art can adopt or not making a free choice within the base knowledge.

Still according to another variation, the centering means can be at the same time also fastening means being composed of bolts engaging threaded bushings incorporated in the cast when it is made. In this case, the casting box constituted by a perfect copy of the bracket and receiving coil assembly 1 must properly have even holes for bolts upon which the internal threaded bushings are screwed before the casting of the cast to incorporate them in the cast in the correct relative position with the bolts. Such bushings may be provided externally with a thread having a direction opposite to the one of the internal thread of the bushings or with a plurality of external radial flaps that are not illustrated in details.

In an alternative to the provision of a casting box separated by the bracket and receiving coil assembly 1, which box is made as a perfect copy of said assembly 1, it is possible that said bracket and receiving coil assembly 1 is itself a part of the casting box. In this case, further wall portions will be provided that can be coupled in a movable way to the supporting bracket and to the receiving coil to complete the casting box enclosing on all sides of the forearm and the hand even in the inner area of the receiving coil. As regards the head sides one can take into consideration what has been said before with regard to the presence on at least a head side of a tight seal quite soft and resilient or a seal as a tight ring that can be swollen and eventually on at least on a side of a head wall that can be tightly coupled with the shell wall.

In this way the casting for forming the cast is made directly on the assembly 1 formed by the supporting bracket and the receiving coil making even more precise the fitting of the complementary contact and reciprocal positioning walls between said assembly and said cast.

Again according to another embodiment not illustrated in detail, the cast that is divided into two halves according to a separation plane parallel to the substantially median plane of the hand that is parallel to the plane defined by the extension of the palm of the hand in wide condition, can be even firmly attachable to a bracket and coil assembly. In this case the supporting bracket can be composed of a shell surface closed on itself similarly to the coil and both said supporting bracket and the coil can be composed of at least two portions having an angular extension of 180° or of three portions having an angular extension of 210° that are hinged one with respect to the other and simultaneously movable to an opened position and to a closed position.

The cast in two or three portions that are complementary and corresponding to said portions hinged one with respect to the other of the supporting bracket and of the coil can be attached in and with each cast portions to the corresponding portions of the supporting bracket and of the coil in a steady manner by means of fastening means such as screws, bolts or the like. Therefore for a patient having a long pathology it is possible to maintain for some time a supporting bracket and receiving coil assembly anatomically dedicated to said patient, without loosing the possibility once the patient is recovered to use again the bracket and the receiving coil for another patient and moreover without loosing the possibility to restore the cast on the bracket and on the receiving coil for the discharged patient when that could be unfortunately necessary.

Figure 4:
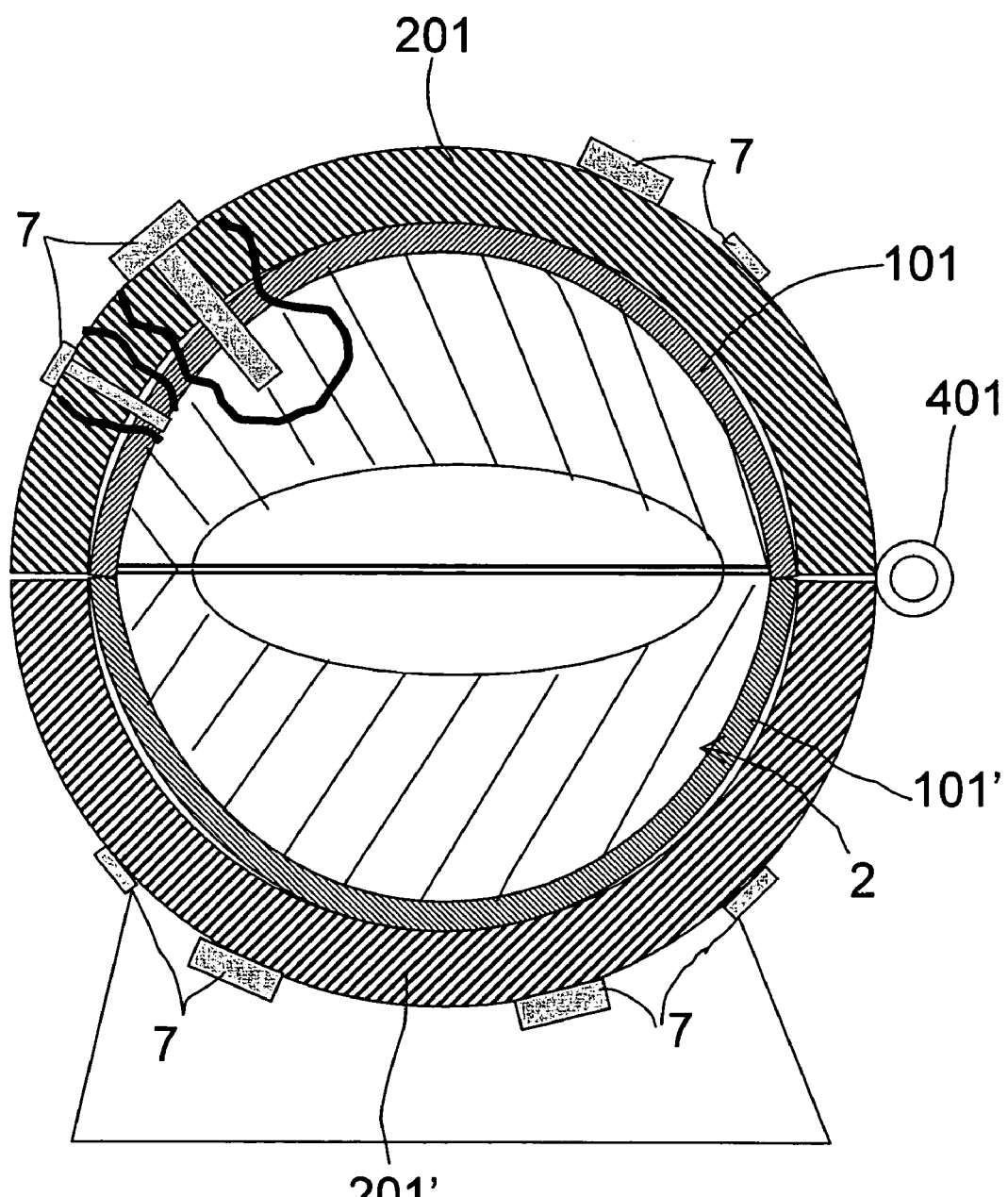
FIGS. 4 and 5 are trasverse sections of a further varying embodiment wherein the bracket, receiving coil and cast assembly is realized in two parts hinged one with respect to the other, in closed and opened position, respectively.
Figure 5:
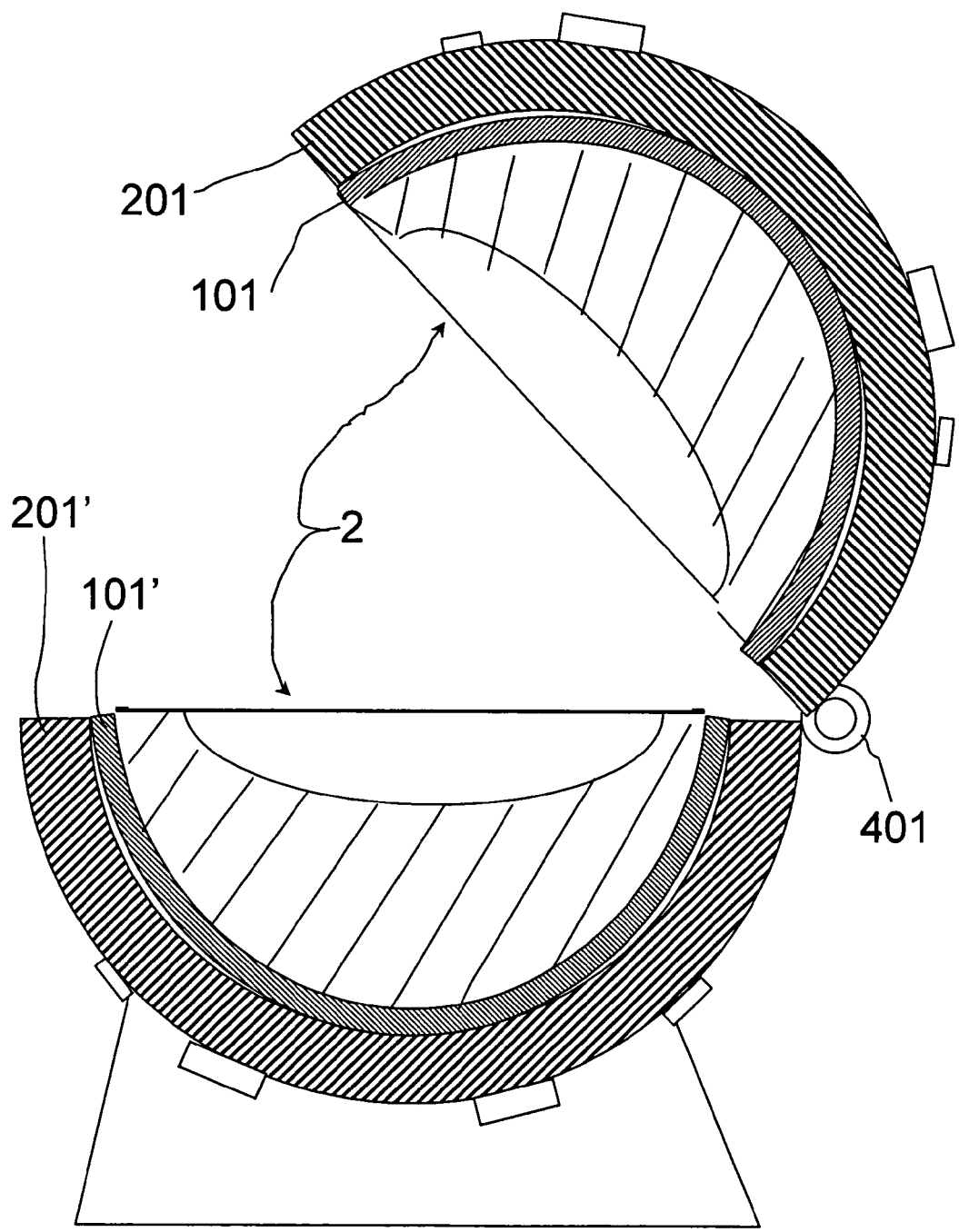

The above is shown in FIGS. 4 and 5. In this embodiment the circular ring of the receiving coil 201 is divided into two halves hinged one with respect to the other at a hinge 401. The ends diametrically opposed may be provided with mechanical engaging means of the two halves of the receiving coil. At said two halves also automatic electric connectors are provided connecting the individual turns of the receiving coil that have been cut off to allow its opening and that can be constituted also by the mechanical connectors connecting the ends of the two coil portions opposite the hinge 401. A tubular shell wall divided into two halves by an axial plane coinciding with the separation axial plane of the two halves of the receiving coil constitutes the housing chamber of the two halves of the cast separated by a separation plane extending at least not fully transversally to the separation planes of the receiving coil and of the tubular member. One of the two halves of the tubular element constitutes the support for the forearm and for the hand indicated with 101 in the preceding figures. The two said halves of the tubular member 101, 101' are attached to the corresponding two halves of the receiving coil 201, while the two cast halves are attached to the receiving coil 201 and to said two halves 101, 101' of the tubular wall. The above fastening is realized by means of bolts or radial pins 7 according to the modes already disclosed. FIG. 4 shows the assembly of the receiving coil of the bracket for the limb and of the cast in the closed condition, while FIG. 5 shows said portions in the opened condition.

The above clearly shows the simplicity and the cheapness and the versatility of the repositioning apparatus according to the present invention.

Even if the described embodiment has been indicated at present as the preferred one, it has not to be considered limitative as regards the general scope of the present invention.

Although only preferred embodiments are specifically illustrated and described herein, it will be appreciated that many modifications and variations of the present invention are possible in light of the above teachings and within the purview of the appended claims without departing from the spirit and intended scope of the invention.

What is claimed is:

1. A method for diagnostic imaging of a body part, by nuclear magnetic resonance, which method comprises the steps of:

positioning the body part in a detection volume of a nuclear magnetic resonance imaging apparatus, inside a dedicated receiving coil;

defining the relative position of the receiving coil with respect to the detection volume by time durable and repeatable positioning references;

defining the relative position of the body part with respect to the receiving coil by time durable and repeatable positioning references:

selecting the section or sections of the body part that is to be imaged and carrying out image detection by nuclear magnetic resonance;

identifying and storing the detected images; and carrying out at intervals one or more subsequent image detections with nuclear magnetic resonance of the same body part and of the same section thereof as in the preceding image detections with nuclear magnetic resonance, positioning each time the body part in the same relative position with respect to the imaging volume of the nuclear magnetic resonance imaging apparatus by the repeatable positioning references of the receiving coil relative to the detection volume and by the repeatable positioning references of the body part to the receiving coil.

2. The method according to claim 1, wherein the method is provided in conjunction with a nuclear magnetic resonance imaging apparatus which is provided with a magnetic structure and gradient and transmitting coils as well as a receiving coil having at least a predetermined position with respect to the magnetic structure and/or the imaging volume, the body part being positioned in the exact position of the preceding image detections thereof with respect to the receiving coil and/or the imaging volume.

3. The method according to claim 1, wherein the method includes administering contrast agents, the selection of the section planes wherein the images have to be detected, the storage of the sequences of nuclear magnetic resonance imaging, of the doses and modes for administering the contrast agents and particularly the definition of the section plane or planes along which the images with nuclear magnetic resonance are detected.

4. The method according to claim 1, wherein the method provides the repositioning of the end limb or part thereof with respect to the receiving coil by means assuring a millimetric positioning repeatability.

5. The method according to claim 1, wherein the method is applied to limbs and/or joints or to a part thereof in the follow up of the course of the rheumatoid arthritis.

6. The method according to claim 1, wherein the method provides the repeatable image detection with nuclear magnetic resonance of the synovial membrane.

7. The method according to claim 1, wherein the method is applied to the hand and/or the wrist.

8. The method according to claim 1, wherein the repeatable positioning references of the body part relative to the receiving coil are the anatomical shape of the body part.

9. The method of claim 8, wherein the repeatable positioning references of the body part relative to the receiving coil are formed by a precise mold of the anatomical shape of at least part of the body part.

10. The method according to claim 1, wherein the method provides the repositioning of the end limb or part thereof with respect to the receiving coil by means assuring a sub-millimetric positioning repeatability.

11. A nuclear magnetic resonance imaging apparatus comprising:
a magnetic structure defining an imaging volume for image detection;
a bracket for supporting a body part; and
a receiving coil;
wherein the bracket and the receiving coil are adapted to be associated in a predetermined relative position repeatable with accuracy to the magnetic structure;
the bracket has a solid matrix on which mechanic counterpart surfaces can be formed, recorded, stored, or modeled that are anatomically complementary to the body part and which surfaces can be formed, recorded, stored, or modeled with respect to the magnetic structure, the imaging volume or the receiving coil or optionally, the bracket has a virtual positioning matrix on which can be recorded or stored anatomical details of the body part with respect to structural details of the magnetic structure or the imaging volume or the receiving coil.

12. A nuclear magnetic resonance imaging apparatus comprising:
a magnetic structure defining an image detection cavity or imaging volume, gradient coils, exciting impulse transmitting coils of nuclear magnetic resonance signals, and a receiving coil, which receiving coil is for accommodating inside it a body part to be imaged;
the magnetic structure or the receiving coil are provided with means for detecting the relative position between the body part and the magnetic structure or receiving coil or imaging volume and for repeatable positioning of said body part in the same relative position with respect to the magnetic structure or the receiving coil or the imaging volume;
wherein said means for detecting the relative position and for repositioning the body part comprise a cast of the body part, which cast can be coupled in a relative steady and repeatable position, with the magnetic structure or the receiving coil;
wherein the cast is made by casting in a die which is comprised of a casting box having at least an opening for the limb and can be tightly closed and said box being made at least partially in a manner identical to the contact surfaces of the cast with the limb supporting bracket and receiving coil assembly.

13. A nuclear magnetic resonance imaging apparatus to claim 12, comprising:
a magnetic structure defining an image detection cavity or imaging volume. gradient coils, exciting impulse transmitting coils of nuclear magnetic resonance signals, and a receiving coil, which receiving coil is for accommodating inside it a body part to be imaged;
the magnetic structure or the receiving coil are provided with means for detecting the relative position between the body part and the magnetic structure or receiving coil or imaging volume and for repeatable positioning of said body part in the same relative position with respect to the magnetic structure or the receiving coil or the imaging volume;
wherein said means for detecting the relative position and for repositioning the body part comprise a cast of the body part, which cast can be coupled in a relative steady and repeatable position, with the magnetic structure or the receiving coil;
wherein the cast is made by casting in a moulding box that is comprised at least partly of the body part supporting bracket and the receiving coil, and a tubular supporting bracket, and is separable at least in two portions and that can be tightly closed at the head sides being provided and an annular receiving coil divisible in two portions substantially along the same separation plane as the tubular supporting bracket and said tubular supporting bracket being provided at least with a casting opening and eventually with at least an air vent.

14. A nuclear magnetic resonance imaging apparatus comprising:
a magnetic structure defining an image detection cavity or imaging volume, gradient coils, exciting impulse transmitting coils of nuclear magnetic resonance signals, and a receiving coil, which receiving coil is for accommodating inside it a body part to be imaged;
the magnetic structure or the receiving coil are provided with means for detecting the relative position between the body part and the magnetic structure or receiving coil or imaging volume and for repeatable positioning of said body part in the same relative position with respect to the magnetic structure or the receiving coil or the imaging volume;
wherein said means for detecting the relative position and for repositioning the body part comprise a cast of the body part, which cast can be coupled in a relative steady and repeatable position, with the magnetic structure or the receiving coil;

wherein the cast comprises two portions that can be divided and coupled, one with respect to the other, and the cast has a symmetry similar to the body part or a shape similar to a geometric simple envelope shape of the body part;

wherein the cast has means for precise positioning and centering the cast with respect to a bracket for supporting the body part and the nuclear magnetic resonance imaging apparatus or with the receiving coil;

wherein the cast is made by casting in a moulding box that is comprised at least partly of the body part supporting bracket and the receiving coil, and a tubular supporting bracket, and is separable at least in two portions and that can be tightly closed at the head sides being provided and an annular receiving coil divisible in two portions substantially alone the same separation plane as the tubular supporting bracket and said tubular supporting bracket being provided at least with a casting opening and eventually with at least an air vent;

wherein holes extend through the coil or the supporting bracket, and fastening bolts project inside the tubular supporting bracket and are inserted and upon which internal threaded bushings are screwed to incorporate in the casting.

15. The apparatus according to claim 14, wherein the threaded bushings have external anchor flaps to the casting or an external knurling or an external thread.

16. The apparatus according to claim 14, wherein the cast is made with plaster or with resin.

17. The apparatus according to claim 14, wherein the cast is cylindrical and the coil is cylindrical or the cast has a transversal elliptical or polygonal section.

18. The apparatus according to claim 17, wherein the supporting bracket of the body part and the receiving coil as well as the supporting bracket of the body part and the closing wall are for housing a hand or a wrist and at least part of a forearm, the box being closed on all sides and can be tightly closed at the had limb introduction side.

19. The apparatus according to claim 14, further comprising a bracket for the cast which is comprised of or attached to the assembly formed by the receiving coil and the supporting bracket of the body part.

20. The apparatus according to claim 14, wherein the cast can be attached to the supporting bracket of the body part or to the coil.

21. The apparatus according to claim 14, wherein the cast has at least two portions, each one has at least part of its external surface shaped in a complementary way to parts of the receiving coil or the supporting bracket of the body part.

22. The apparatus according to claim 14, wherein the at least two cast portions are integrated in the constructional assembly of the supporting bracket of the body part and the receiving coil.

23. The apparatus according to claim 14, wherein at least the receiving coil is made with two portions that can be attached and disassembled one with respect to the other to each coil portion being joined or attachable to the cast, the surfaces of the two coil portions and those of the two portions being shaped and oriented one with respect to the other in such a way that disassembling the two coil portions one with respect to the other automatically involves the separation of the cast, while attaching the two coil portions involves the closing of the cast itself.

24. The apparatus according to claim 23, wherein the two coil portions are hinged one with respect to the other and can be moved to the closing position of the coil and to the opening position of the coil, corresponding to the simultaneous opening of the cast and to the simultaneous closing of the cast.

25. The apparatus according to claim 23, wherein the receiving coil is an annular one and the supporting bracket of the body part is composed of a cradle that is substantially coaxial to the receiving coil and is attached to at least one of the two portions of the receiving coil.

26. The apparatus according to claim 25, wherein the supporting bracket of the body part is tubular and is coaxial to the receiving coil, said tubular supporting bracket being divided into two portions according to a separation plane corresponding substantially to the one of the two portions of the receiving coil and to each one of said two portions of the supporting bracket being attached or attachable to a corresponding cast portion all this in such a way that the closing of the receiving coil involves the approach of the two portions of the tubular bracket and the closing of the two cast portions one against the other, while opening the coil involves also the opening of the tubular bracket and of the cast.

* * * * *